United States Patent
Derible et al.

[11] 3,988,453
[45] Oct. 26, 1976

[54] NOVEL PHENOTHIAZINES AS NEUROLEPTICS

[75] Inventors: Pierre Henri Derible, Le Perreux; Jean-Paul Lavaux, Paris; Jacques Laurent, Chilly-Mazarin, all of France

[73] Assignee: Roussel-UCLAF, Paris, France

[22] Filed: Sept. 9, 1975

[21] Appl. No.: 611,711

Related U.S. Application Data
[62] Division of Ser. No. 539,639, Jan. 9, 1975, Pat. No. 3,923,800.

[30] Foreign Application Priority Data
Jan. 21, 1974 France .............................. 74.01880

[52] U.S. Cl. ............................................. 424/247
[51] Int. Cl.² ......................................... A61K 31/54
[58] Field of Search ................................... 424/247

*Primary Examiner*—Stanley J. Friedman
*Attorney, Agent, or Firm*—Hammond & Littell

[57] ABSTRACT

Novel phenothiazines of the formula

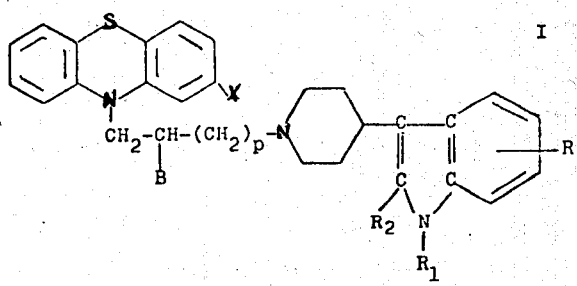

wherein X is selected from the group consisting of hydrogen, chlorine, trifluoromethyl, methylthio and methoxy, B is selected from the group consisting of hydrogen and alkyl of 1 to 3 carbon atoms, $p$ is 0 or 1, R is selected from the group consisting of hydrogen and alkoxy of 1 to 3 carbon atoms and $R_1$ and $R_2$ are individually selected from the group consisting of hydrogen and alkyl of 1 to 3 carbon atoms and their non-toxic, pharmaceutically acceptable acid addition salts having neuroleptic activity and frequently antihistaminic activity and their preparation.

13 Claims, No Drawings

NOVEL PHENOTHIAZINES AS NEUROLEPTICS

PRIOR APPLICATION

This application is a division of our copending, commonly assigned U.S. application Ser. No. 539,639 filed Jan. 9, 1975, now U.S. Pat. No. 3,923,800.

STATE OF THE ART

Commonly assigned U.S. patent application Ser. No. 407,995 filed Oct. 19, 1973, discloses 10-(piperidinoalkyl) phenothiazines which are substituted in the 4-position of the piperidino group with a substituted alkoxy group which possess neuroleptic, analgesic, spasmolytic and antihistaminic activity.

OBJECTS OF THE INVENTION

It is an object of the invention to provide the novel phenothiazines of formula I and their non-toxic, pharmaceutically acceptable acid addition salts and a novel process for their preparation.

It is another object of the invention to provide novel neuroleptic compositions.

It is a further object of the invention to provide a novel method of inducing neuroleptic activity in warm-blooded animals.

These and other objects and advantages of the invention will become obvious from the following detailed description.

THE INVENTION

The novel phenothiazines of the invention are selected from the group consisting of compounds of the formula

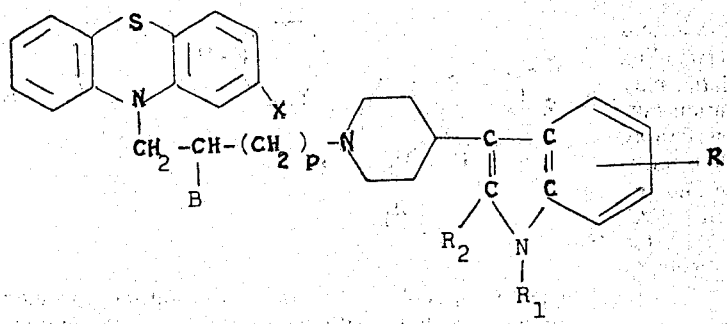

wherein X is selected from the group consisting of hydrogen, chlorine, trifluoromethyl, methylthio and methoxy, B is selected from the group consisting of hydrogen and alkyl of 1 to 3 carbon atoms, $p$ is 0 or 1, R is selected from the group consisting of hydrogen and alkoxy of 1 to 3 carbon atoms and $R_1$ and $R_2$ are individually selected from the group consisting of hydrogen and alkyl of 1 to 3 carbon atoms and their non-toxic, pharmaceutically acceptable acid addition salts.

In the compounds of formula I, the alkyl of 1 to 3 carbon atoms may be methyl, ethyl, propyl or isopropyl for example and the alkoxy of 1 to 3 carbon atoms could be methoxy or ethoxy for example.

Among the preferred substituents of formula I, X is trifluoromethyl, B is hydrogen or methyl and $p$ is 1. In another preferred group of compounds, X is trifluoromethyl, B and $R_1$ are hydrogen and $p$ is 1.

Among the preferred compounds of the invention are 4-(3'-indolyl)-1-[γ-(10''-phenothiazinyl)-propyl]-piperidine and its hydrochloride; 4-(3'-indolyl)-1-[γ-(2''-trifluoromethyl-10''-phenothiazinyl)-propyl]-piperidine and its hydrochloride; 4-(6'-methoxy-2'-methyl-3'-indolyl)-1-[γ-(2''-trifluoromethyl-10''-phenothiazinyl)-propyl]-piperidine and its hydrochloride; and 4-(3'-indolyl)-1-[β-methyl-γ-(2''-trifluoromethyl-10''-phenothiazinyl)-propyl]-piperidine and its hydrochloride.

Examples of suitable acids for the non-toxic, pharmaceutically acceptable acid addition salts are inorganic acids such as hydrochloric acid, hydrobromic acid, hydroiodic acid, nitric acid, sulfuric acid and phosphoric acid and organic acids such as acetic acid, formic acid, benzoic acid, maleic acid, fumaric acid, succinic acid, tartaric acid, citric acid, oxalic acid, glyoxylic acid, aspartic acid, alkysulfonic acids and arylsulfonic acids.

The novel process of the invention for the preparation of the phenothiazines of formula I comprises reacting a compound of the formula

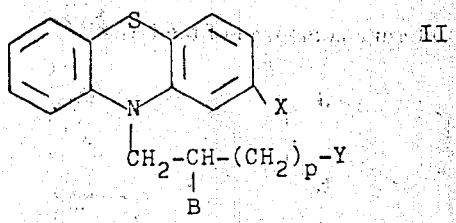

wherein X, B and $p$ have the above definitions and Y is chlorine or bromine with an indole derivative of the formula

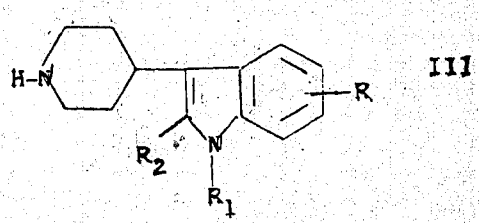

wherein R, $R_1$ and $R_2$ have the above definitions to form the corresponding compound which can then be reacted with an acid to form the acid addition salt.

In a preferred embodiment, the reaction is effected in an inert organic solvent such as amyl alcohol or methyl ethyl ketone in the presence of an alkaline agent such as sodium carbonate, potassium carbonate or triethylamine to act as acid acceptor for the acid formed in the reaction.

In a variant of the process of the invention, a compound of the formula

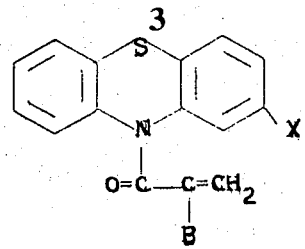

wherein X and B have the above definition is reacted with an indole of the formula

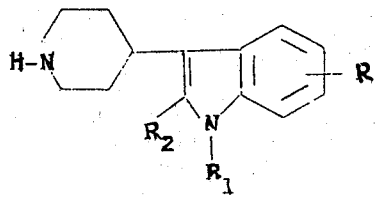

to form a compound of the formula

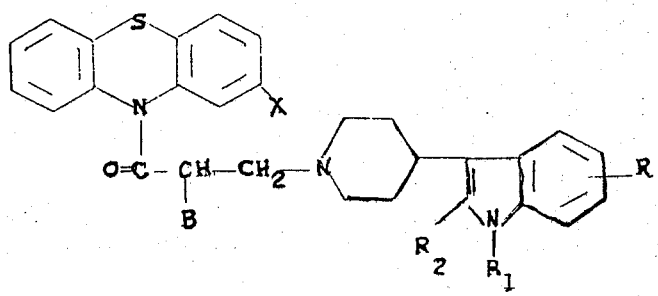

and reducing the latter with aluminum chloride and lithium aluminum hydride to form the corresponding compound of formula I where p is 1 and the latter may be reacted with an acid to form the acid addition salt.

In the latter process, the first reaction is preferably effected in an anhydrous organic solvent such as tetrahydrofuran at reflux of the reaction mixture and the reduction is effected in tetrahydrofuran at 0° to 10° C.

The indoles of formula III may be prepared by the process of Belgium Pat. No. 802,912 by reacting benzyl bromide with a compound of the formula

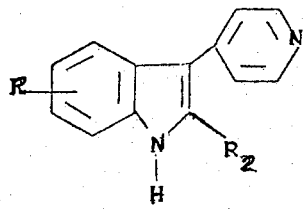

to form a compound of the formula

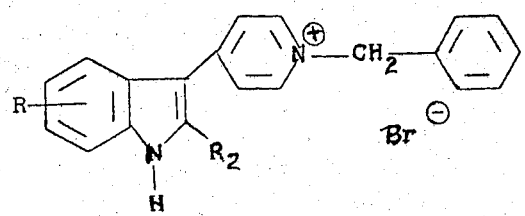

and reducing the latter with sodium borohydride to obtain a compound of the formula

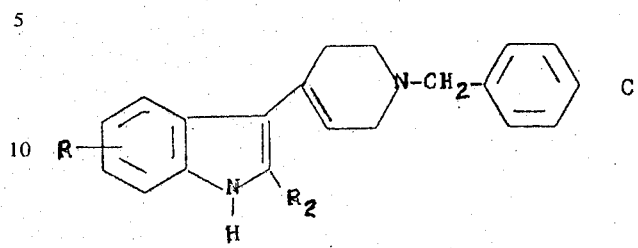

either reducing the compound with gaseous hydrogen in the presence of a palladium based catalyst to form a compound of formula III in which $R_1$ is hydrogen or reacting a compound of formula C with an alkyl halide wherein the alkyl is $R_1$ in the presence of sodium hydride to form a compound of the formula

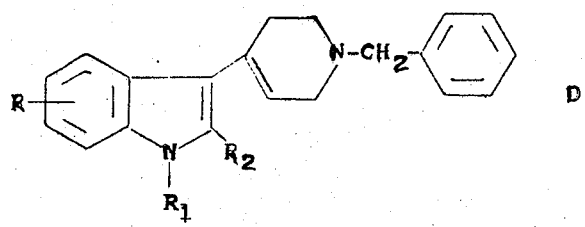

wherein $R_1$ is alkyl of 1 to 3 carbon atoms and then reducing the latter with gaseous hydrogen in the presence of a palladium based catalyst to form a compound of Formula III wherein $R_1$ is alkyl of 1 to 3 carbon atoms.

A variant of the process permits the preparation of a new intermediate for the preparation of compounds of formula I wherein X is methoxy, B is methyl and p is 1 and the said intermediate is 2-methoxy-10-(α-methylacryloyl)-phenothiazine.

The compounds of formula IV which are not known may be prepared by reacting a compound of the formula

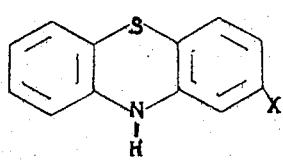

with an acid chloride of the formula

wherein X and B have the above definition in an organic solvent such as toluene.

The novel neuroleptic compositions are comprised of an effective amount of at least one compound of formula I and their non-toxic, pharmaceutically acceptable acid addition salts and a pharmaceutical carrier.

The compositions may be in the form of tablets, dragees, gelules, granules, suppositories or injectable solutions or suspensions prepared in the usual manner.

The active ingredients may be incorporated into the usual excipients for pharmaceutical compositions such as talc, gum arabic, lactose, amidon, magnesium stearate, cacao butter, aqueous or non-aqueous vehicles, fats of animal or vegetable origin, paraffinic derivatives, glycols, preservations, various wetting agents, dispersants or emulsifiers.

The neuroleptic compositions have a kinetic action which is differed and prolonged and some of the products also possess antihistaminic activity. Depending upon the specific products, method of administration and the test used, the beginning of the effect is more or less rapid (generally a few hours) and the duration of the effect is more or less prolonged (several hours, days or even weeks).

The neuroleptic compositions are useful for the treatment in humans of chronic psychoses, of schizophenia, of delirious or hallucinatory syndromes, of chronic mania, of manic-depressive psychoses, of oligophrenia, of character and behaviour troubles as well as for the treatment of diverse allergic manifestations.

The novel method of the invention for inducing neuroleptic activity in warm-blooded animals comprises administering to warm-blooded animals an effective amount of at least one compound of formula I and its non-toxic, pharmaceutically acceptable acid addition salts. The compounds may be administered orally, rectally or parenterally and the usual effective daily dose is 0,2 to 5 mg/kg depending upon the product, of the method of administration. The period between administration may be a few days up to a few weeks.

In the following examples there are described several preferred embodiments to illustrate the invention. However, it should be understood that the invention is not intended to be limited to the specific embodiments.

EXAMPLE 1

4-(3'-indolyl)-1-[γ-(10''-phenothiazinyl)-propyl]-piperidine.HCl

A mixture of 6.3 g of 10-(γ-chloropropyl)-phenothiazine and 4 g of 3-(4'-piperidyl)-indole in 60 ml of amyl alcohol was refluxed for 10 hours and the mixture was evaporated to dryness. The residue was chromatographed over silica gel and was eluted with methylene chloride containing 5% methanol to obtain 4 g of 4-(3'-indolyl)-1-[γ-(10''-phenothiazinyl)-propyl]-piperidine. The said product was dissolved in ether and the solution was treated with a solution of hydrochloric acid in ether. The precipitate formed was crystallized from refluxing ether containing 3% methanol and the mixture was filtered. The precipitate was dried to obtain 3.8 g of 4-(3'-indolyl)-1-[γ-(10''-phenothiazinyl)-propyl]-piperidine hydrochloride in the form of white crystals melting at 200° C.

Analysis: $C_{29}H_{30}ClN_3S$

| | %C | %H | %N | %S | %Cl |
|---|---|---|---|---|---|
| Calculated: | 70.59 | 6.35 | 8.83 | 6.73 | 7.45 |
| Found: | 70.8 | 6.4 | 8.8 | 6.8 | 7.5 |

EXAMPLE 2

4-(3'-indolyl)-1-[γ-(2''-trifluoromethyl-10''-phenothiazinyl)-propyl]-piperidine hydrochloride 17.19 g of 10-(γ-chloropropyl)-2-trifluoromethylphenothiazine in 100 ml of methyl ethyl ketone were added to a refluxing suspension of 10 g of 3-(4'-piperidinyl)-indole and 7.5 g of sodium iodide in 150 ml of methyl ethyl ketone and reflux was continued for 24 hours. The mineral residue was filtered off and the filtrate was concentrated to dryness. The oil residue was dissolved in methylene chloride and the solution was washed with an aqueous sodium bicarbonate solution and then with water, was dried and concentrated to dryness. The residue was dissolved in ether and the solution was filtered. The filtrate was evaporated to dryness to obtain 17.2 g of 4-(3'-indolyl)-1-[γ-(2''-trifluoromethyl-10''-phenothiazinyl)-propyl]-piperidine in the form of an oil.

The oil was dissolved in ether and the solution was treated with activated carbon and filtered. The filtrate was added to hydrochloric acid in ether and the mixture was filtered. The product was crystallized from a methanol-acetone mixture to obtain 13.4 g of 4-(3'-indolyl)-1-(2''-trifluoromethyl-10''-phenothiazinyl)-propyl]-piperidine hydrochloride in the form of white crystals melting at 154° C.

Analysis: $C_{29}H_{29}ClF_3N_3S$

| | %C | %H | %Cl | %F | %N | %S |
|---|---|---|---|---|---|---|
| Calculated: | 64.01 | 5.37 | 6.51 | 10.47 | 7.72 | 5.89 |
| Found: | 64.1 | 5.5 | 6.3 | 10.5 | 7.4 | 5.6 |

EXAMPLE 3

4-(5'-methoxy-3'-indolyl)-1-[γ-(2''-trifluoromethyl-10''-phenothiazinyl)-propyl]-piperidine hydrochloride STEP A: 4-(5'-methoxy-3'-indolyl)-piperidine A mixture of 11 g of 4-(5'-methoxy-3'-indolyl)-piperidine, 9.5 g of benzyl bromide and 120 ml of ethyl acetate was refluxed for 4 hours and after cooling the mixture was filtered. The recovered precipitate was washed with ethyl acetate and dried under reduced pressure to obtain 17.5 g of 1-benzyl-4-(5'-methoxy-3'-indolyl)-pyridinium bromide melting at 254° C.

3.5 g of sodium borohydride were added in small amounts at 40° C to a mixture of 17.5 g of 1-benzyl-4-(5'-methoxy-3'-indolyl)-pyridinium bromide in 150 ml of methanol and 65 ml of water and after stirring the mixture at room temperature for 24 hours; 150 ml of water were added thereto. The precipitate formed was recovered by vacuum filtration, was washed with water, dried and crystallized from methanol to obtain 13 g of 1-benzyl-4-(4'-methoxy-3'-indolyl)-1,2,3,6-tetrahydropyridine in the form of a cream white solid melting at 168° C.

A mixture of 12.5 g of 1-benzyl-4-(5'-methoxy-3'-indolyl)-1,2,3,6,-tetrahydropyridine and 3 g of 10% palladized carbon in 300 ml of ethanol was heated to 50° C while passing hydrogen therein and 1770 ml of hydrogen were absorbed in 7 hours. After the reaction was complete, the catalyst was filtered off and the filtrate was evaporated to dryness under reduced pressure to obtain 8.3 g of 4-(5'-methoxy-3'-indolyl)-piperidine in the form of white crystals melting at 170° C.

STEP B: 4-(5'-methoxy-3'-indolyl)-1-[γ-(2''-trifluoromethyl-10''-phenothiazinyl)-propyl]-piperidine hydrochloride A suspension of 8 g of 2-trifluoromethyl-10-(γ-chloropropyl)-phenothiazine, 4.3 g of 4-(5'-methoxy-3'-indolyl)-piperidine and 3 g of sodium carbonate in 60 ml of amyl alcohol containing a trace of hydroquinone was refluxed for 15 hours and the solvent was then evaporated. The residue was chromatographed over silica gel and was eluted with an 85–15 methylene chloride-methanol mixture to obtain 8.7 g of 4-(5'-methoxy-3'-indolyl)-1-[γ-(2''-trifluoromethyl-10''-phenothiazine)-propyl]-piperidine in the form of an oil. The oil was taken up in hydrochloric acid in ether and the mixture was filtered. The recovered precipitate was crystallized from ethyl acetate to obtain 6.5 g of 4-(5'-methoxy-3'-indolyl)-1-[γ-(2''-trifluoromethyl-10''-phenothiazinyl)-propyl]-piperidine hydrochloride in the form of white crystals melting at 145° C.

to obtain 34 g of a product in the form of brown crystals which were crystallized from acetonitrile to obtain 19.5 g of 4-(2'-methyl-6'-methoxy-3'-indolyl) -pyridine in the form of brown yellow crystals melting at 196°–198° C and slightly soluble in acetonitrile and benzene.

A mixture of 3.4 g of 4-(2'-methyl-6'-methoxy-3'-indolyl)-pyridine and 2.65 g of benzyl bromide in 30 ml of ethyl acetate was refluxed for 4 hours and after cooling the mixture was vacuum filtered. The recovered yellow crystals were washed with ethyl acetate and dried to obtain 5.7 g of 1-benzyl-4-(2'-methyl-6'-methoxy-3'-indolyl)-pyridinium bromide in the form of yellow crystals melting at 244°–246° C.

1 g of 1-benzyl-4-(6'-methoxy-2'-methyl-3'-indolyl)-pyridinium bromide in 165 ml of methanol was added to 70 ml of water at 35°–40° C and after cooling to 25° C, 4 g of sodium borohydride were added thereto in small amounts while keeping the temperature below 30°–35° C. The mixture was stirred for 2 hours at room temperature and then water was added thereto. The precipitate formed was recovered by vacuum filtration, was washed with water and dried under reduced pressure to obtain 15.4 g of 1-benzyl-4-(2'-methyl-6'-methoxy-3'-indolyl)-1,2,3,6-tetrahydropyridine in the form of orange crystals melting at 142°–143° C.

24 g of 1-benzyl-4-(2'-methyl-6'-methoxy-3'-indolyl)-1,2,3,6-tetrahydropyridine, 4 g of 10% palladized carbon and 300 ml of absolute ethanol was heated to 50° C and hydrogen was introduced. After 12 hours, 2450 ml of hydrogen had been absorbed and the catalyst was filtered off. Another 3.0 g of 10% palladized carbon was added to the hydrogenation chamber and the reaction was continued for 3 ½ hours during which 3250 ml of hydrogen were absorbed. The catalyst was filtered off and ethanol was evaporated from Analysis: $C_{30}H_{31}ClF_3N_3OS$
Calculated: %C 62.76, %H 5.44, %N 7.32, %Cl 6.18, %F 9.93, %S 5.59
Found: 62.6, 5.5, 7.00, 6.3, 9.9, 5.5

EXAMPLE 4

4-(2'-methyl-6'-methoxy-3'-indolyl)-1-[γ-(2''-trifluoromethyl-10''-phenothiazinyl)-propyl]-piperidine hydrochloride STEP A: 4-(2'-methyl-6'-methoxy-3'-indolyl)-piperidine 87 g of benzoyl chloride were added dropwise to a mixture of 50 g of 2-methyl-6-methoxy-indole in 230 ml of pyridine cooled to −40° C and the mixture was stirred in the dark at room temperature for 3 days. The pyridine was evaporated under reduced pressure and the residue was washed with an aqueous sodium hydroxide solution and the water was evaporated. The pasty product was dissolved in 500 ml of refluxing methanol and 200 ml of sodium hydroxide followed by 200 ml of water were added thereto with stirring. The mixture was stirred for 2 hours and allowed to stand overnight after which the methanol was evaporated under reduced pressure. The aqueous phase was extracted with chloroform and the organic phase was dried over sodium sulfate and evaporated to dryness under reduced pressure to obtain 100 g of raw product. The product was chromatographed over alumina and was eluted with benzene. The benzene was evaporated the filtrate under reduced pressure to obtain 16.6 g of 4-(2'-methyl-6'-methoxy-3'-indolyl)-piperidine in the form of white crystals melting at 166° C. The crystals were soluble in absolute ethanol and slightly soluble in acetonitrile.

STEP B: 4-(2'-methyl-6'-methoxy-3'-indolyl)-1-[γ-(2''-trifluoromethyl-10''-phenothiazinyl)-propyl]-piperidine hydrochloride A mixture of 5 g of 4-(2'-methyl-6'-methoxy-3'-indolyl)-piperidine, 7.5 g of 2-trifluoromethyl-10-(γ-chloropropyl)-phenothiazine, 1.5 g of potassium carbonate and 100 ml of amyl alcohol was refluxed for 5 hours and after the addition of another 1.5 g of potassium carbonate, the mixture was refluxed for another 3 hours. 200 ml of methylene chloride were added thereto and the mixture was chromatographed over silica gel. Elution was with a 1-9 methanol-methylene chloride mixture and evaporation of the solvents gave an oily residue which was taken up in ether. Hydrochloric acid in ether was added thereto and the resulting precipitate was crystallized from ether, vacuum filtered and dried to obtain 4.2 g of 4-(2'-methyl-6'-methoxy-3'-indolyl)-1-[γ-(2''-trifluoromethyl-10''-phenothiazinyl)-propyl]-piperidine hydrochloride in the form of white crystals melting at 200° C.

Analysis: $C_{31}H_{33}N_3OSClF_3$
Calculated: %C 63.3 %H 5.66 %N 7.15 %S 5.45 %Cl 6.02 %F 9.7
Found: 63.0 5.6 7.3 5.1 6.4 10.0

EXAMPLE 5

4-(3'-indolyl)-1'-[γ-(2''-chloro-10''-phenothiazinyl)-propyl]-piperidine hydrochloride A mixture of 4 g of 4-(3'-indolyl)-piperidine, 8 g of 2-chloro-10-(γ-chloropropyl)-phenothiazine, 4.5 g of potassium carbonate, 0.7 g of potassium iodide and 200 ml of amyl alcohol was refluxed for 20 hours and then 200 ml of a solution of 5% potassium carbonate in water were added. The mixture was decanted and the organic phase was evaporated. The residue was dissolved in methylene chloride and a precipitate was formed by addition of cyclohexane to the solution to obtain 7.5 g of 4-(3'-indolyl)-1-[γ-(2''-chloro-10''λ phenothiazinyl)-propyl]-piperidine in the form of a gum. The gum was taken up in ether and hydrochloric acid in ether was added thereto to obtain a gum. The latter was crystallized from dioxane and was treated with refluxing ether containing 2 to 3% of methanol to obtain 2 g of 4-(3'-indolyl)-1-[γ-(2''-chloro 10''-phenothiazinyl)-propyl]-piperidine hydrochloride in the form of cream crystals melting at 240° C.

27 g of 2-trifluoromethyl-phenothiazine and 12 g of α-methylacryloyl chloride in 100 ml of toluene were 1 for 2 hours and the mixture was evaporated to dryness. The residue was chromatographed over silica gel and elution with a 1—1 benzene-cyclohexane mixture gave 18 g of 2-trifluoromethyl-10-(α-methyl acryloyl)-phenothiazine in the form of white crystals melting at 103°C.

A mixture 6 g of 2-trifluoromethyl-10-(α-methyl acryloyl)-phenothiazine, 8 g of 4-(3'-indolyl)-piperidine and 30 ml of tetrahydrofuran was refluxed with stirring for 24 hours and after stopping the heating, the mixture was stirred for 3 days. The precipitate was taken up in methylene chloride and the mixture was filtered. The filtrate was evaporated to dryness and the residue was chromatographed over silica gel. Elution with an 85–15 methylene chloride-ethanol mixture yielded 4-(3'-indolyl)-1-[1''-(2'''-trifluoromethyl-10''λ''-phenothiazinyl)-2''-methyl-3''-propionyl]-piperidine. The said product was treated with hydrochloric acid in ether to obtain 8.7 g of the corresponding hy- Analysis: $C_{28}H_{29}N_3SCl_2$; molecular weight = 510.54
Calculated: %C 65.87 %H 5.73 %N 8.28 %S 6.28 %Cl 13.89
Found: 65.5 5.7 8.3 6.2 14.3

EXAMPLE 6

4-(3'-indolyl)-1-[γ-(2''-methoxy-10''-phenothiazinyl)-propyl]-piperidine hydrochloride A mixture of 6.7 g of 2-methoxy-10-(γ-chloropropyl)phenothiazine, 4 g of 4-(3'-indolyl)-piperidine, 0.5 g of potassium iodide, 4 g of potassium carbonate and 100 ml of amyl alcohol was refluxed for 5 hours and the reaction mixture was then washed with distilled water until the wash waters were neutral. The organic phase was evaporated to dryness and the residue was chromatographed over silica gel. Elution with a 95–5 methylene chloride-methanol mixture yielded 4 g of 4-(3'-indolyl)-1-[γ-(2''-methoxy-10''-phenothiazinyl)-propyl]-piperidine. The said product was dissolved in dioxane and addition of hydrochloric acid in ether formed a precipitate. The product was crystallized from ether containing 2% of methanol and then ether to obtain 4.3 g of 4-(3'-indolyl)-1-[γ-(2''-methoxy-10''-phenothiazinyl)-propyl]-piperidine hydrochloride in the form of cream crystals melting at 195° C.

drochoride salt in the form of white crystals melting at 176° C.

STEP B: 4-(3'-indolyl)-1-[β-methyl-γ-(2''-trifluoromethyl-10''-phenothiazinyl)-propyl]-piperidine hydrochloride 50 ml of tetrahydrofuran were added under an inert atmosphere and with strong cooling to 2.7 g of lithium aluminum hydride and the 9 g of aluminum chloride were added thereto in small amounts with continued cooling. Then, a solution of 8 g of 4-(3'-indolyl)-1-[1''-(2'''-trifluoromethyl-10'''-phenothiazinyl)-2''-methyl-3''-propionyl]-piperidine in 50 ml of tetrahydrofuran was added thereto dropwise at 0° C and then ethylacetate and a saturated sodium sulfate solution was added over about 2 hours. The mixture was filtered and the filtrate was washed with ethanol and concentrated to dryness to obtain 6 g of 4-(3'-indolyl)-1-[β-methyl-γ-(2''-trifluoromethyl-10''-phenothiazinyl)-propyl]-piperidine. The said product was taken up in ether to which was added hydrochloric acid in ether. The product was chromatographed over silica gel and was eluted Analysis: $C_{29}H_{30}ClN_3OS$
Calculated: %C 68.82 %H 6.37 %N 8.3 %Cl 7.0 %S 6.33
Found: 68.70 6.40 8.3 7.2 6.3

EXAMPLE 7

4-(3'-indolyl)-1-[β-methyl-γ-(2''-trifluoromethyl-10''-phenothiazinyl)-propyl]-piperidine hydrochloride with a 95–5 methylene chloride-ethanol mixture to obtain 2.9 g of the corresponding hydrochloride salt in the form of cream crystals melting at 200° C.

Analysis: $C_{30}H_{31}ClF_3N_3S$
Calculated: %C 64.56 %H 5.61 %Cl 6.4 %N 7.53 %F 10.2 %S 5.7
Found: 64.1 5.8 6.6 7.5 10.2 5.7

STEP A: 4-(3'-indolyl)-1-[1''-(2'''-trifluoromethyl-10'''-phenothiazinyl)-2''-methyl-3''-propionyl]-piperidine hydrochloride

EXAMPLE 8

4-(3'-indolyl)-1-[γ-(2''-methoxy-10''-phenothiazinyl)-β-methyl propyl]-piperidine hydrochloride STEP A: 4-(3'-indolyl)-1-[1''-(2'''-methoxy-10'''-phenothiazinyl) -2''-methyl-3''-propionyl]-piperidine hydrochloride A mixture of 23 g of 2methoxy-phenothiazine, 21 g of methacryloyl chloride and 120 ml of toluene was refluxed for 3 hours and was then cooled and washed with 250 ml of N sodium hydroxide. The organic phase was decanted and the aqueous phase was washed twice with 50 ml of toluene. The combined organic phases were washed with water, dried over magnesium sulfate, treated with carbon black and evaporated to dryness to obtain 29.6 g of 2-methoxy-10-(α-methyl acryloyl)-phenothiazine melting at 91°–92° C.

A mixture of 6.5 g of 2-methoxy-10-(α-methyl acryloyl) -phenothiazine, 8 g of 4-(3'-indolyl)-piperidine and 30 ml of tetrahydrofuran containing 0.15 g of hydroquinone was refluxed -methyl-for 36 hours and was then concentrated to dryness. The residue was taken up in methylene chloride and the solution was filtered. The filtrate was evaporated to dryness and the residue was chromatographed over silica gel and was eluted with methylene chloride and then methylene chloride containing 10% of ethanol to obtain 9 g of 4-(3'-indolyl)-1-[1''-(2'''-methoxy-10'''-phenothiazinyl)-2''-methyl-l3''-propionyl]-piperidine in the form of an oil which was treated with hydrochloric acid in ether to form the corresponding hydrochloride salt melting at 220° C.

STEP B: 4-(3'-indolyl)-1-[γ-(2''-methoxy-10''-phenothiazinyl) -β-methyl-propyl]-piperidine hydrochloride 50 ml of tetrahydrofuran were added under an inert atmosphere and with stirring at −30° C to 1.7 g of lithium aluminum hydride and 6 g of aluminum chloride were added in small amounts to the mixture at −30° C. The mixture was stirred for 10 minutes at −10° C and then a solution of 6.5 g of 4-(3'-indolyl)-1-[1''-(2'''-methoxy-10'''-phenothiazinyl)-2''methyl-3''-propionyl]-piperidine in 50 ml of tetrahydrofuran was added thereto. The mixture was stirred for 2 ½ hours at room temperature and after cooling to −10° C, 10 ml of ethyl acetate followed by 30 ml of water and 200 ml of 2 N hydrochloric acid were added thereto. The aqueous phase was washed with ether, made alkaline and was extracted with chloroform. The organic phase was evaporated to dryness under reduced pressure to obtain 4.5 g of 4-(3'-indolyl)-1-[γ-(2''-methoxy-10''-phenothiazinyl)-β-methyl-propyl]-piperidine in the form of an oil. The oil was taken up in hydrochloric acid in ether and the solvent was distilled off. The residue was crystallized from acetonitrile to obtain 2 g of the corresponding hydrochloride salt melting at 188°C.

EXAMPLE 9

Tablets were prepared from 20 mg of 4-(3'-indolyl)-1-[γ-(2''-trifluoromethyl-10''-phenothiazinyl)-propyl]-piperidine hydrochloride or 25 mg of 4-(3'-indolyl-1-[γ-(2''-methoxy-10''-phenothiazinyl)-propyl]-piperidine hydrochloride with an excipient of lactose, amidon, talc and magnesium stearate.

An injectable aqueous suspension was prepared from 10 mg of 4-(3'-indolyl)-1-[γ-(2''-trifluoromethyl-10''-phenothiazinyl)-propyl]-piperidine hydrochloride, 10 mg of benzyl alcohol, 8 mg of sodium chloride, 7 mg of emulsifiers and sufficient distilled water to have 1 ml of the suspension.

PHARMACOLOGICAL DATA

The differed and prolonged acting neuroleptic properties and the antihistaminic activity of the compounds of formula I were studied in the following tests.

A. Antagonism to stereotypes provoked by apomorphine

This test was conducted on groups of 5 male rats in individual cages with the procedure of Janssen et al [Arzn. Forsch., Vol. 15 (1965), p. 104–117 and Vol. 17 (1967), p. 841–854]. Each rat orally received the test compound and then, at variable times, an intraveinous injection of 1.5 mg of apomorphine hydrochloride in the veins of the penis. The times of injection were 1 hour, 24 hours, 2 days, 3 days or 4 days after the test product administration and the rats were studied during 1 minute after 5,10 and 15 minutes after the injection and the stereotype movements of the jaws spheres were evaluated for their degree of intensity on a scale for 0 to 3 /Boissier et al, Therapie, Vol. 25 (1970), p. 939–949/. The ED₅₀ was determined at the maximum of the effect for the time considered that is to say the dose reducing the symptoms by 50% in the treated animals as compared to control animals and the results are reported in Table I.

B. Antagonism to toxicity provoked by amphetamine

This test was effect on groups of 10 male mice grouped in crystallizers with a 20 cm diameter and a 9 cm height closed with a grilled lid. Each mouse orally received a determined dose of the test product and at different times a single intraperitoneal dose of dexamphetamine sulfate. The injection was effected 1 hour, 24 hours or 2,3,4 or 7 days after the administration of the test compound and the mortality for each group was determined 24 hours after the injection. The ED₅₀, the dose at which the toxicity of dexamphetamine sulphate was reduced by 50%, was determined and the results are reported in Table I.

Analysis: $C_{30}H_{34}N_3ClOS$; Molecular weight = 520.15
Calculated: %C 69.27 %H 6.59 %N 8.08 %Cl 6.82 %S 6.16
Found: 69.2 6.5 8.0 6.7 6.1

TABLE I

| Product of Example | Apomorphine Sterotypes | | | | | Amphetaminic Toxicity | | | | |
|---|---|---|---|---|---|---|---|---|---|---|
| | 1 h | 24 h | 2 d | 3 d | 4 d | 1 h | 24 h | 2 d | 3 d | 4 d | 7 d |
| 1 | >50 | 35 | | | | <10 | <10 | | | | |
| 2 | >50 | <10 | 18 | 17 | 33 | <10 | <10 | <10 | 50 | | |
| 3 | >50 | <10 | <10 | 12 | 20 | <10 | <10 | <10 | <10 | <10 | |
| 4 | >50 | 9 | 9 | 16 | 25 | 10 | <10 | <10 | 9 | 9 | 50 |
| 5 | >50 | <10 | 12 | 27 | | 16 | <10 | <10 | 10 | 17 | |
| 6 | >50 | <10 | 45 | | | <10 | <10 | 10 | | | |
| 7 | >20 | 10 | 10 | <10 | 12 | >20 | <10 | <10 | 13 | <10 | 19 |
| 8 | >50 | <10 | 12 | 30 | | <10 | <10 | <10 | 18 | | |

The results of Table I show that the products of the invention when orally administered have important neuroleptic properties appearing more or less rapidly after the products are administered and the activity has a prolonged duration.

C. Antagonism to stereotypes provoked by amphetamine

This test with the product of Example 2 was effected on groups of 5 rats with the rats individually held in cages and after the rats received intraperitoneally or subcutaneously an aqueous suspension of the product at a dose of 10 mg/kg, each rat received intraperitoneally at different times a single injection of 8 mg/kg of dexamphetamine sulfate. The second injections were made 1 hour or 1,3 or 7 days after the first injection and the results were determined by the procedure of Halliwel et al [Brit. J. Pharmacol., Vol. 23 (1964), p. 330-350]. The percentage of protection was determined and the results are reported in Table II.

TABLE II

| Method of Administration | % Protection After | | | |
|---|---|---|---|---|
| | 1 hour | 1 day | 3 days | 7 days |
| Intraperitoneal | 39 | 77 | 68 | 61 |
| Subcutaneous | 17 | 84 | 60 | 14 |

Table II shows that the product of Example 2, when injected intraperitoneally or subcutaneously, has an important antagonistic effect of prolonged duration against the stereotypes provoked by amphetamine.

D. Antagonism against vomiting provoked by apomorphine

This test was effected on 3 dogs on whom the number of vomits provoked by a single subcutaneous injection of 0.1 mg/kg of apomorphine hydrochloride 8 days before this test. Each dog received subcutaneously an injection of an aqueous suspension of 0.3 mg/kg or 0.8 mg/kg of the product of Example 2 and an injection of 0.1 mg/kg of apomorphine hydrochloride 30 minutes, 7 days, 14 days, 21 days, 28 days, 35 days and 42 days thereafter. The percentage of protection was determined for each time interval and the results are reported in Table III.

TABLE III

| Dose in mg/kg | % of protection after | | | | | | |
|---|---|---|---|---|---|---|---|
| | 30 min. | 7 d | 14 d | 21 d | 28 d | 35 d | 42 d |
| 0.3 | 24 | 86 | 57 | 29 | 10 | | |
| 0.8 | 0 | 100 | 95 | 84 | 79 | 42 | 21 |

Table III shows that the product of Example 2 has an important prolonged neuroleptic activity.

E. Antihistaminic Activity

This test was effected on guinea pigs which received orally a single dose of 10 mg/kg of the test product and then a intraveinous injection of 0.8 mg/kg of histamine hydrochloride 1 hour or 24 hours thereafter. This histamine dose is the minimum lethal dose for 100% of the animals within about 3 minutes and after 10 minutes, any surviving animals were considered to be protected. Each product was rated to see if 50% of the animals were alive at this dose and the values of Table IV show at least 50% protected by + and less than 50% protected by 0.

TABLE IV

| Product of Example | Protection After | |
|---|---|---|
| | 1 hour | 24 hours |
| 1 | 0 | + |
| 2 | + | 0 |
| 5 | + | + |
| 6 | 0 | + |
| 7 | 0 | + |
| 8 | 0 | + |

Table IV shows that the products of the invention possess, when orally administered, an important antihistaminic activity which rapidly appears and is relatively prolonged.

F. Acute toxicity

The acute toxicity of the product of Example 2 was determined on groups of 10 mice of the Swiss strain weighing about 20 g receiving increasing doses orally or intraperitoneally of the test product. The mortality was determined 72 hours after the product administration. The $LD_{50}$ was about 300 mg/kg intraperitoneally and greater than 1600 mg/kg orally.

Various modifications of the products and methods of the invention may be made without departing from the spirit or scope thereof and it is to be understood that the invention is to be limited only as defined in the appended claims.

We claim:

1. A neuroleptic composition comprising an effective amount of a active compound selected from the group consisting of a compound of the formula

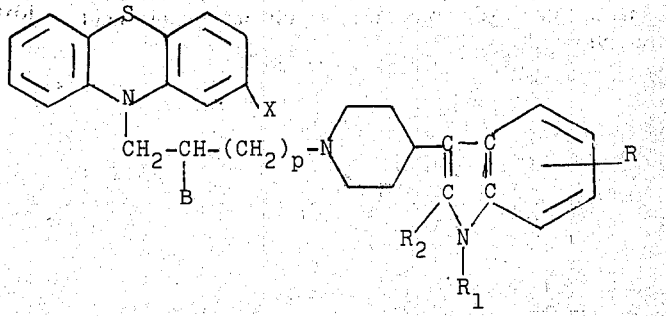

wherein X is selected from the group consisting of hydrogen, chlorine, trifluoromethyl, methylthio and methoxy, B is selected from the group consisting of hydrogen and alkyl of 1 to 3 carbon atoms, p is 0 or 1, R is selected from the group consisting of hydrogen and alkoxy of 1 to 3 carbon atoms and $R_1$ and $R_2$ are individually selected from the group consisting of hydrogen and alkyl of 1 to 3 carbon atoms and its non-toxic, pharmaceutically acceptable acid addition salt and a carrier.

2. A composition of claim 1 wherein the active compound is selected from the group consisting of 4-(3'-indolyl)-1-[γ-(2''-trifluoromethyl-10''-phenothiazinyl)-propyl]-piperidine and its non-toxic, pharmaceutically acceptable acid addition salt.

3. A method of inducing neuroleptic activity in warm-blooded animals comprising administering to warm-blooded animals a neuroleptically effective amount of an active compound selected from the group consisting of a compound of the formula

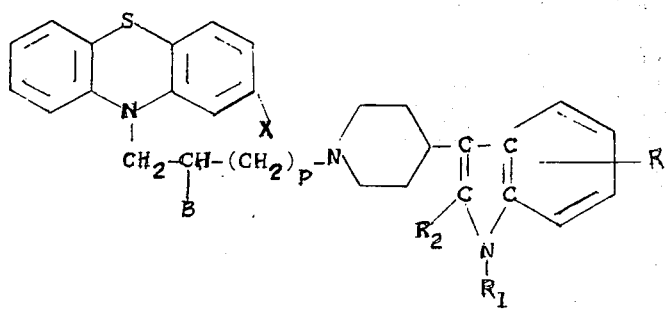

wherein X is selected from the group consisting of hydrogen, chlorine, trifluoromethyl, methylthio and methoxy, B is selected from the group consisting of hydrogen and alkyl of 1 to 3 carbon atoms, p is 0 or 1, R is selected from the group consisting of hydrogen and alkoxy of 1 to 3 carbon atoms and $R_1$ and $R_2$ are individually selected from the group consisting of hydrogen and alkyl of 1 to 3 carbon atoms and its non-toxic, pharmaceutically acceptable acid addition salt.

4. The method of claim 3 wherein the active compound is selected from the group consisting of 4-(3'-indolyl)-1-[γ-(2''-trifluoromethyl-10''-phenothiazinyl)-propyl]-piperidine and its non-toxic, pharmaceutically acceptable acid addition salt.

5. The method of claim 3 wherein X is —CF$_3$, p is 1 and B is selected from the group consisting of hydrogen and methyl.

6. The method of claim 3 wherein X is —CF$_3$, p is 1 and B and $R_1$ are hydrogen.

7. The method of claim 3 wherein the active compound is selected from the group consisting of 4-(3'-indolyl)-1-[γ-(10''-phenothiazinyl)-propyl]-piperidine and its non-toxic, pharmaceutically acceptable acid addition salt.

8. The method of claim 3 wherein the active compound is selected from the group consisting of 4-(5'-methoxy-3'-indolyl)-1-[γ-(2''-trifluoromethyl-10''-phenothiazinyl)-propyl]-piperidine and its non-toxic, pharmaceutically acceptable acid addition salt.

9. The method of claim 3 wherein the active compound is selected from the group consisting of 4-(2'-methyl-6'-methoxy-3'-indolyl)-1-[γ-(2''-trifluoromethyl-10''-phenothiazinyl)-propyl]-piperidine and its non-toxic, pharmaceutically acceptable acid addition salt.

10. The method of claim 3 wherein the active compound is selected from the group consisting of 4-(3'-indolyl)-1-[γ-(2''-chloro-10''-phenothiazinyl)-propyl]-piperidine and its non-toxic, pharmaceutically acceptable acid addition salt.

11. The method of claim 3 wherein the active compound is selected from the group consisting of 4-(3'-indolyl)-1-[γ-(2''-methoxy-10''-phenothiazinyl)-propyl]-piperidine and its non-toxic, pharmaceutically acceptable acid addition salt.

12. The method of claim 3 wherein the active compound is selected from the group consisting of 4-(3'-indolyl)-1-[γ-(2''-methoxy-10''-phenothiazinyl)-β-methyl-propyl]-piperidine and its non-toxic, pharmaceutically acceptable acid addition salt.

13. The method of claim 3 wherein the active compound is selected from the group consisting of 4-(3'-indolyl)-1-[γ-(2''-trifluoromethyl-10''-phenothiazinyl)-β-methyl-propyl]-piperidine and its non-toxic, pharmaceutically acceptable acid addition salt.

* * * * *